United States Patent
Irion et al.

(10) Patent No.: US 6,361,490 B1
(45) Date of Patent: Mar. 26, 2002

(54) TESTING AND/OR SETTING DEVICE FOR A PHOTODYNAMIC DIAGNOSIS OR THERAPY SYSTEM, OR FOR TRAINING ON SUCH A SYSTEM

(75) Inventors: Klaus Irion, Liptingen; Andre Ehrhardt, Tuttlingen; Clemens Rebholz, Uhldingen-Mühlhofen, all of (DE); Karl-Heinz Strobl, Fiskdale, MA (US)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/254,984
(22) PCT Filed: Sep. 22, 1997
(86) PCT No.: PCT/DE97/02138
§ 371 Date: Mar. 17, 1999
§ 102(e) Date: Mar. 17, 1999
(87) PCT Pub. No.: WO98/11945
PCT Pub. Date: Mar. 26, 1998

(30) Foreign Application Priority Data

Sep. 20, 1996 (DE) .......................................... 196 38 809

(51) Int. Cl.$^7$ ............................. A61B 1/00; G01N 21/00
(52) U.S. Cl. ...................... 600/175; 434/267; 73/865.9; 600/160
(58) Field of Search ................................. 600/101, 102, 600/117, 118, 181, 407, 175; 250/372; 73/1.56, 865.6, 865.9, 866.4; 356/51; 434/267, 272

(56) References Cited

U.S. PATENT DOCUMENTS 5,045,704 A  * 9/1991 Coates ..................... 356/445
5,820,547 A  * 10/1998 Stohl et al. .............. 600/127

* cited by examiner

*Primary Examiner*—John P. Leubecker
(74) *Attorney, Agent, or Firm*—St. Onge Steward Johnston & Reens LLC

(57) ABSTRACT

A device for testing and/or adjusting a PDD or PDT system and/or for training on such a system comprises an illumination system emitting light which serves at least to stimulate a fluorescent dye and which may be directed to this end onto a tissue zone to be diagnosed and/or therapeutically treated, and an imaging unit which images the light arriving from the stimulated tissue zone. The invention is characterized by the provisions that a target is provided which reflects the light of the illumination system, and that the target comprises at least one light source which emits light within the wavelength range of the fluorescence spectrum of the dye.

24 Claims, 2 Drawing Sheets

TESTING AND/OR SETTING DEVICE FOR A PHOTODYNAMIC DIAGNOSIS OR THERAPY SYSTEM, OR FOR TRAINING ON SUCH A SYSTEM

DESCRIPTION

1. Field of the Invention

The present invention relates to a device for testing and/or adjusting a PDD or PDT system and/or for training on such a system.

2. Prior Art

Systems for photodynamic diagnosis (PDD) and/or photodynamic therapy (PDT) are employed in medicine in many ways and forms. Just by way of example ophthalmologic, endoscopic or neuro-surgical applications should be mentioned here.

The photodynamic diagnosis and therapy serves, for instance, to detect or treat malignant and also benign degenerations. To this end, photosensitising substances are administered which collect specifically in the tissue to be analysed and which fluoresce in response to illumination with stimulating light (photodynamic diagnosis) or, respectively, produce a photo-toxic effect when the photosensitising substance is administered in high doses and a high intensity of illumination is provided, which effect destroys the degenerated tissue (photodynamic therapy). Endogenous fluorescent substance can also be used for photodynamic diagnosis. Then so-called auto-fluoresceins are involved.

The range of wavelength of the stimulating light includes shorter wavelengths than the range in which fluorescent light occurs.

In the known PDD or PDT systems the problem is involved that the fluorescence, which characterises the tissue and which is induced by the administered photosensitising substance and by the application of stimulating light, can be detected only "in vivo". This means that presently the known PDD or PDT systems can be completely tested or verified in their entirety only under "in vivo" conditions.

Moreover, at present training or education on PDD or PDT systems can be provided only "in vivo" as well. This involves the inevitable acceptance of either a comparatively high burden on the patients part or insufficient training with the consequence that malignant tissue or carcinomas, respectively, are possibly not detected.

The present invention is therefore based on the problem of providing a device which is suitable for "ex vivo" testing of PDD or PDT systems and/or training on such systems.

An inventive solution to this problem is defined in Patent claim 1. Improvements of the invention are the subject matters of claims 2 et seq.

BRIEF DESCRIPTION OF THE INVENTION

In accordance with the invention a device is provided for testing and/or adjusting a PDD or PDT system and/or for training on such a system, which comprises a target reflecting the light from the illuminating system of the PDD or PDT system, and at least one light source emitting the light within the wavelength range of the fluorescent spectrum of the respective photosensitising substance.

The inventive device hence allows for both testing of the illuminating system and the imaging unit of the PDD or PDT system. It is possible, in particular, that the manufacturer of such a system checks such a system for functional integrity, inclusive of fluorescence detection, prior to delivery of the system to a customer. The system can also be employed to adjust the individual components and specifically to check the adjustment of a possibly envisaged filter system.

Above all, however, the inventive device permits the training of physicians for the application of such systems, enabling the doctors to convince themselves of the unobjectionable condition of the used PDD system in the event of a negative result.

Within the general framework of the basic inventive idea, the most different embodiments are conceivable:

It is possible, for instance, that the target includes several light sources so that the light emitted within the wavelength range of the fluorescent spectrum of the respective photosensitising substance comes from a "larger area". Specifically in an approach to offer certain patterns to the trainee on such a PDD or PDT system for recognition, it is possible to control the light sources selectively in such a manner that they emit light in the form of definable patterns. Additionally or alternatively the size of the light-emitting area of the light sources may be varied.

Furthermore, the light sources may present emission surfaces of different sizes, which may be used, inter alia, to detect an extension of fluorescent areas which is just still detectable by the examining person. Hence the limits of resolution can be determined.

For adjustment of the system it is moreover preferable that the target includes at least one sensor which detects the intensity of the illuminating light and produces an output signal which is applied to a controller which controls the intensity of the light emitted by the light source or sources. In order to convey to the trainee on such a PDD or PDT system an "idea" of the mode of operation of such a system it is moreover expedient that the at least one sensor detects the intensity of the illuminating light only within that wavelength range by which the respectively employed photosensitiser is stimulated. It is furthermore possible that the controller controls the light source(s) of the target in such a way that these light sources emit light at a reduced brightness, as the time increases, thus simulating the decay of the efficiency of the fluorescent marker.

In a number of PDD or PDT systems the illuminating unit emits not only light within the wave range by which the photosensitiser is stimulated but also in other wavelength ranges so that the irradiated tissue may be additionally illuminated. In an alternative, a further light source or additional light sources may be provided which emit illuminating light in addition to the stimulating light. In such PDD or PDT systems it is preferable that a filter system is provided which blocks the stimulating light which is directly reflected on the tissue zone or the target, so that it is easier for the examining person to detect the fluorescent radiation against the "background" of the irradiated light.

This filter system may be configured, in particular, in correspondence with a design proposed by Karl Storz GmbH & Co. in such a way that the filter system matches the degree of net transmittance of the illuminating system with the fluorescent spectrum of stimulation of the respective photosensitiser and the degree of net transmittance of the imaging unit with the fluorescent spectrum of the respective photosensitiser in such a way that the two degrees of net transmittance will noticeably overlap only within a comparatively narrow wavelength range. This small wavelength range may be selected in particular in such a manner that the light reflected therein will furnish a sufficient "background illumination" for the fluorescent light so that the examining person will be able to "recognise" the illuminated tissue area independently of the fluorescent light.

The visual detectability of the fluorescent radiation can be further enhanced by the provision that the intensity and/or extension of the wavelength range of the light serving merely for illumination may be adjusted. This adjustment can be performed, for instance, by the measure that a light source is used which can be tuned in terms of wavelengths or that a tunable filter system is disposed ahead of the light source with a fixed emission spectrum.

The transmission graph of this filter system may be adjustable like the transmission graph of the filter system of the imaging unit The use of filters in the imaging unit may furthermore be utilised in the following manner:

Particularly in cases where light of a further wavelength range is coupled in additionally to the stimulating light, which serves for background illumination for the range from which fluorescent light is emitted, a differentiation by colour with higher contrast can be obtained by an appropriate selection of the filters or by adjustment of the filter wavelengths.

The inventive device can hence also be employed for detecting the optical colour differentiation between the fluorescent effect and the background light. Moreover, users of a PDD system can utilise the inventive device for the purpose to adjust the system to that respective colour contrast which is subjectively strongest.

It is moreover possible to insert change-over filters into the optical path of the image-transmitting unit. When these filters are change over at a high frequency it is possible to even further increase the contrast between the fluorescent radiation and the background illumination reflected on the tissue or the target, respectively. When the imaging unit includes a video camera it is preferable that the filter change-over be effected at a frequency which corresponds to 1/n times (n=1 . . . 200) of the video frequency.

In any case it is expedient that the target reflects the light of the illuminating system at least in that part of the spectrum which serves to stimulate the photosensitising substance approximately light the body tissue onto which the light of the illuminating system is to be directed. To this end the target may present a surface structure which corresponds roughly to the structure of the tissue to be simulated, specifically in terms of colour and roughness. It is hence possible to test PDD or PDT systems under realistic conditions and to set in particular the contrast of the obtained image by appropriate adjustment of filter systems or emission spectra.

The adaptation of the target to the respective body tissue to be analysed may filter element for wavelength-selective reflection ahead of the surface including the light source(s), in the direction of incidence of the illuminating light.

The inventive device is suitable for testing of or training on any PDD or PDT system whatsoever. The application of inventive devices is, however, particularly expedient in combination with PDD or PDT systems where additional light is coupled in as well for background illumination or for illumination of the fluorescent zone. Such systems may specifically include an endoscope or a surgical microscope into which the illuminating the stimulating light are coupled and which includes an imaging system which constitutes part of the imaging unit. The application of such PDD or PDT systems covers almost the entire range of medicine and is appropriate in particular in endoscopic examination methods or surgery, in ophthalmologic treatment or in neurosurgery.

The devices required to this end are preferably tested with an inventive device which includes a cavity for receiving the distal end of the respective endoscope or microscope lens to be used for testing and/or training. Thus the endoscope or the microscope may be tested under realistic conditions and particularly under light conditions such as those prevailing also inside the body.

It is moreover preferable to introduce a sterile film into the cavity for protection of the inserted element from contamination. In this manner it is possible to test endoscopes or surgical microscopes even during a surgical operation without impairment of the sterility of these parts.

The approximation of the test or training programme performed with the inventive device to reality is even further enhanced when the target presents a curvature in correspondence with the curvature of the object field or the imaging unit. This is, as a rule, the curvature of the organ into which the endoscope is introduced or which is visually examined with the surgical microscope.

The light source or sources of the target may be provided in the most different configurations and types:

For instance, light-emitting diodes or miniature lamps may be provided. It is moreover possible that the light sources are spaced from the target surface rather than being arranged therein. The light of the light source is passed via light-conducting fibres into the target surface where the exit facets of the light-conducting surfaces of the light-conducting fibres are located. It is furthermore possible to dispose a monitor screen or the like in the target surface.

In all of these solutions it is advantageous, however, that the emission spectrum of the light sources be matched with the fluorescent spectrum of the respective photosensitising substance. This adaptation may be made, for instance, by means of a filter system introduced into the optical path of the imaging unit, which filters the light of the light sources in such a way that the image of the target has a spectrum at the proximal end which is at least approximately identical with the fluorescent spectrum of the respective photosensitiser or the endogenous fluorescent substance, respectively.

A controller and analyser unit may be provided to control the various functions, inclusive of the control of the intensity of the light emitted by the light source or sources of the target. This controller and analyser unit, which may be a commercial PC with appropriate additional boards, for instance, is able to control the individual functions in correspondence with a definable programme sequence and to perform training programmes, in particular. Moreover, the signals of the various sensors provided and particularly a video sensor such as a video chip of the imaging unit may be applied to the controller and analyser unit.

BRIEF DESCRIPTION OF THE DRAWING

The invention will be described by exemplary embodiments in the following, without any restriction of the general inventive idea, with reference to the drawing which is explicitly referred to in all other respects as far as the disclosure of all inventive details is concerned which are not fully explained in the text. In the drawing.

DESCRIPTION OF EMBODIMENTS

Figure 1:
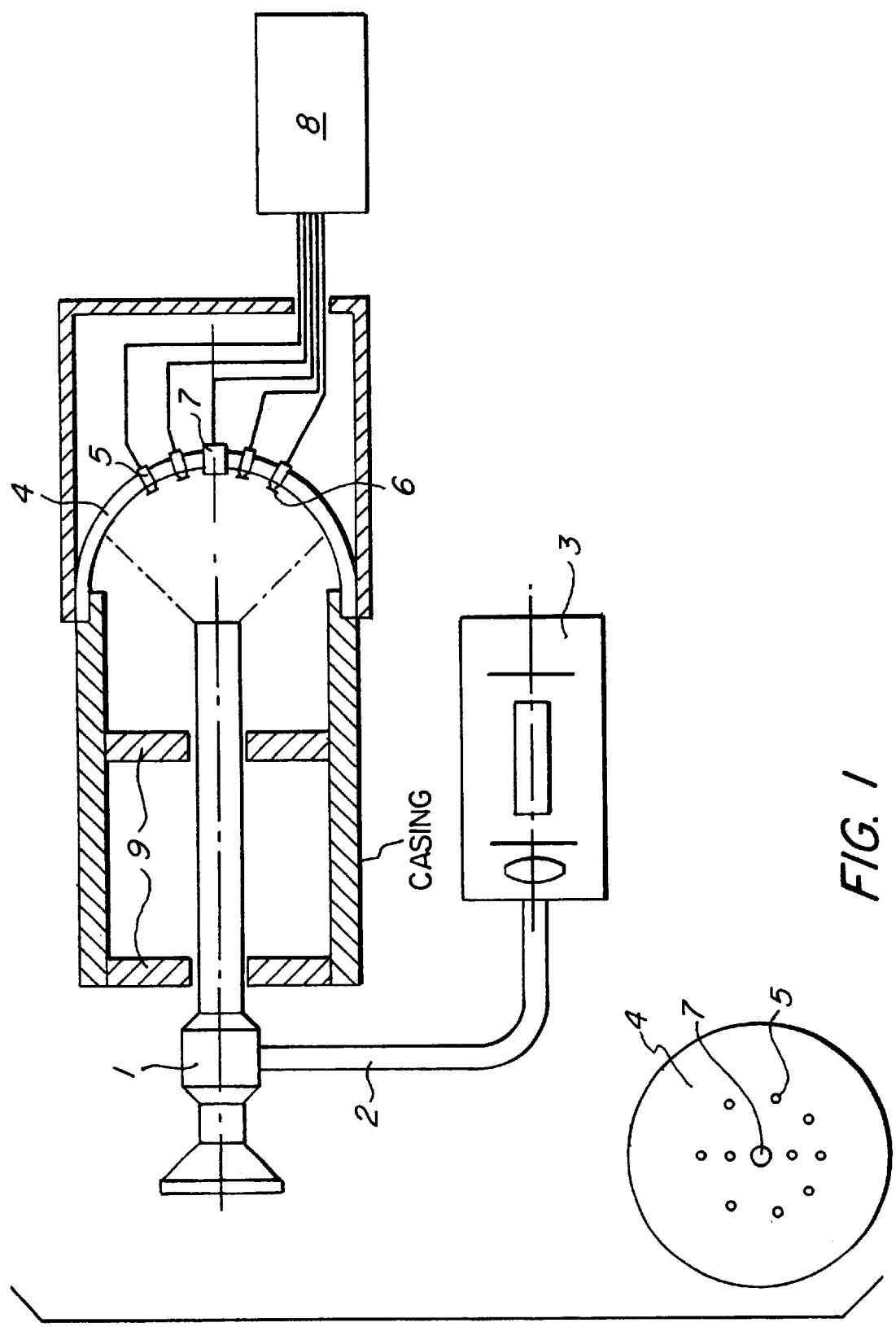
FIG. 1 illustrates an inventive device.

FIG. 1 is a cross-sectional view of an inventive device for testing and/or adjusting PDD or PDT systems or for training on such systems. In the illustrated embodiment the imaging unit, which produces the image of the light arriving from the stimulated tissue zone, is a rigid endoscope 1, without any restriction of the general inventive idea. The endoscope 1 includes a lens in a manner known per se, which is not illustrated here, a relay lens system and an eyepiece for viewing the image generated by the lens disposed on the distal end, which is transmitted by the relay lens system to the proximal end. As an alternative to a visual representation or with use of a beam splitter in addition to visual representation, a video camera may be flange-mounted to the eyepiece as well, equally in a manner known per se. Moreover, the endoscope 1 included an illumination light guide, which is not shown either, with a light guide port which is connected to a PDD or PDT light system 3 via a flexible light guide 2. The light system 3 comprises at least one illumination system emitting light which serves at least to stimulate the fluorescent substance and preferably a light system for illuminating the environment, which emits a light which does not produce a stimulating effect. The light system 3 may include several coherent or incoherent light sources or a wide-band light source which serves two purposes, i.e. the stimulation of the fluorescent dye and illumination of the environment. Such a wide-band light source is manufactured, for instance, by Karl Storz GmbH & Co. In Tuttlingen/Germany. The inventive device includes a target 4 which reflects the light incident thereupon from the light system 3 and which has reflecting properties which are matched with the reflection characteristics of the tissue under examination. In the target 4 several light sources 5 are provided which may be light-emitting diodes, miniature lamps or the light exit facets of light-guiding fibres. For adaptation of the emission spectrum of the light sources to the emission spectrum of the fluorescence marker filters 6 are disposed ahead of the light sources for realising an appropriate spectral adjustment. Moreover, a photo element 7 is arranged in the target 4, which detects the intensity of the illuminating light, particularly in the wavelength range photo element 7 is applied to a controller unit 8 which controls the light intensity of the light sources 5. In addition, the controller 8 is able to control the light sources 5 selectively in such a way that they emit light in the form of definable patterns. The illustration segment in the left bottom in FIG. 1 shows a plan view onto the target 4 for clearly illustrating the position of the light sources 5 and the photo element 7.

Moreover, the inventive device comprises clamping elements 9 for mounting the endoscope 1 inserted therein and for holding it. The clamping elements 9 are so configured that they co-operate with the target 4 for forming a cavity so that the endoscope may be tested under "conditions of practical application" or that training may be provided on the PDD or PDT system under the conditions of practical application.

In the following the mode of operation of the inventive device will be described.

Figure 2:
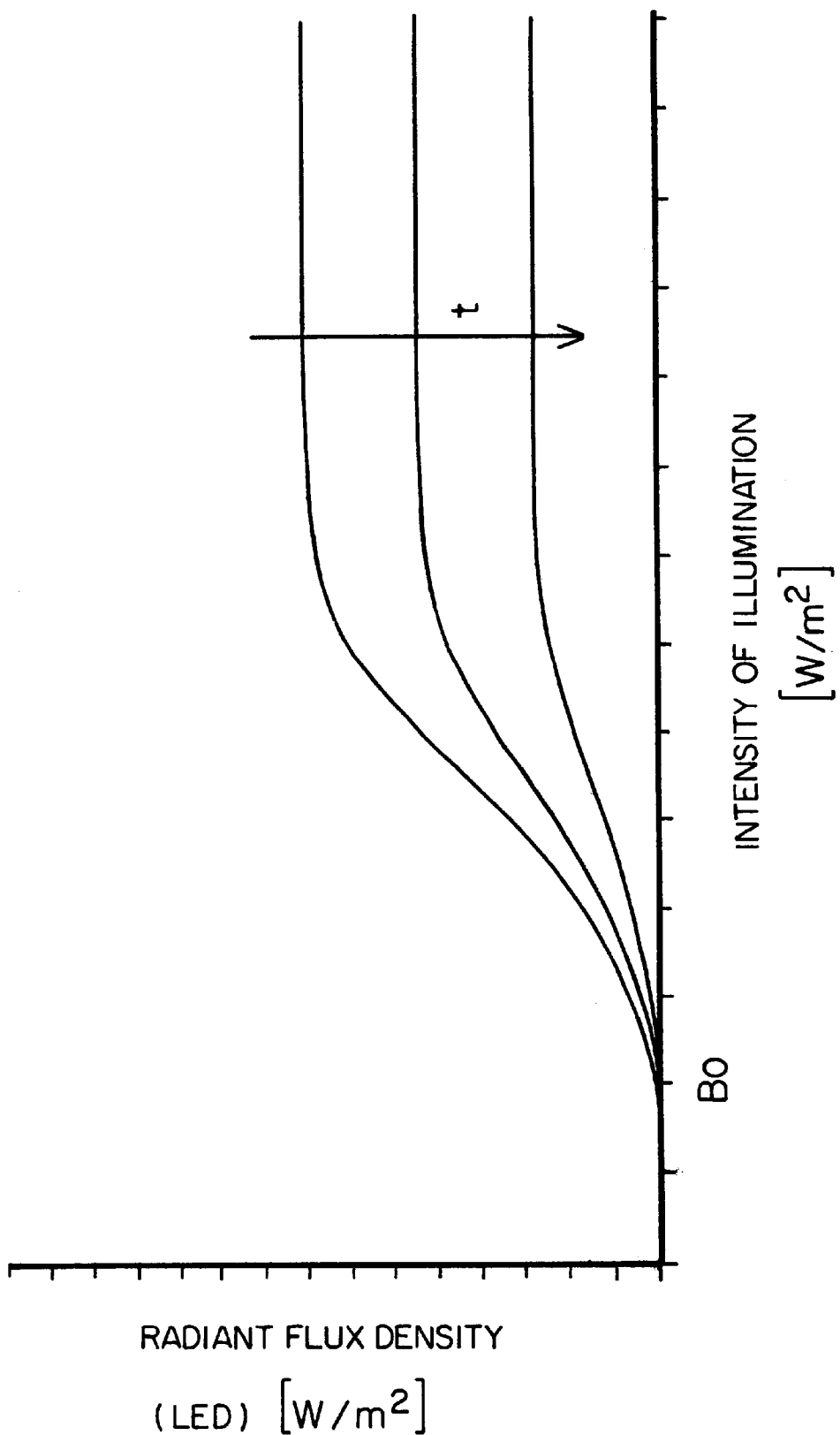
FIG. 2 shows the dependence of the power density of the emitting light sources on the intensity of illumination of the stimulating light.

The photo element 7 detects the mean intensity of illumination (B) of the stimulating light. The controller 8, to which the output signal of the photo element 7 is applied, now controls the light sources 5 in such a way that their emission performance (Lab) is a function of the illumination B of the stimulating light. FIG. 2 is a graph of possible functional curves which serve to reproduce the fluorescent effect in the tissue as "naturally" as possible:

In this embodiment the power density of the light-emitting diodes, which are used as light sources 5, is plotted as a function of the intensity of illumination. It is evident from the Figure that the light-emitting diodes 5 emit light only from a defined threshold BO onwards and from an approximately linear proportional part onwards become "saturated" as the intensity of illumination is further increased. The value of saturation is a function of time and is reduced in the course of time in correspondence with the "consumption of the fluorescent dye" so as to allow for dosimetric simulation.

When amino-laevulinic acid (ALA) is employed as fluorescent dye it is preferable to have the stimulating light within the wavelength range about 410 nm±25 nm, and to provide for light emission by the light-emitting diodes with a wavelength of roughly 635 nm.

What is claimed is:

1. Device for simulating a chosen body tissue zone which contains a particular fluorescent dye and is subjected to illuminating light having a first wavelength range which includes light of a second wavelength range which stimulates said particular dye to emit fluorescent light having a third wavelength range;

wherein said device comprises a target which receives and reflects said illuminating light and is provided with at least one light source which has a light-emitting area which emits light having a wavelength within said third wavelength range.

2. Device according to claim 1, wherein said target includes a plurality of light sources.

3. Device according to claim 2, wherein said at least one light source is selectively controlled in such a way that it emits light in the form of definable patterns.

4. Device according to claim 3, wherein the size of the light-emitting area of said at least one light source is variable.

5. Device according to claim 2, wherein said at least one light source includes light emitting areas of different sizes.

6. Device according to claim 1, wherein said target comprises at least one sensor which detects an intensity of the illuminating light and produces an output signal applied to a controller which controls an intensity of the light emitted by said at least one light source.

7. Device according to claim 6, wherein said at least one sensor detects an intensity of the illuminating light within said second wavelength range.

8. Device according to claim 1, wherein said target reflects said illuminating light in at least said second wavelength range approximately as it would be reflected by said chosen body tissue zone.

9. Device according to claim 8, wherein said target has a surface color and roughness which correspond approximately to that of said chosen body tissue zone.

10. Device according to claim 1, wherein said target comprises a wavelength-selective reflecting surface or a filter element positioned in front of an area including said at least one light source.

11. Device according to claim 1, wherein a cavity is provided for inserting a distal end of an endoscope or a microscope objective lens used as part of an imaging unit for forming an image of said target with light arriving from said target.

12. Device according to claim 11, wherein a sterile film may be placed into said cavity for protecting an inserted distal end of an endoscope or microscope objective lens from contamination.

13. Device according to claim 11, wherein said target has a curvature corresponding to that of an object field curvature of said imaging unit.

14. Device according to claim 1, wherein said at least one light source is a light-emitting diode.

15. Device according to claim 1, wherein said at least one light source is a miniature lamp.

16. Device according to claim 1, wherein said at least one light source is a video screen.

17. Device according to claim 1, wherein said at least one light source is the exit facet of a light guide.

18. Device according to claim 1, wherein a filter system is disposed in front of said at least one light source, which matches the spectrum of said at least one light source to the fluorescence spectrum of said particular fluorescent dye.

19. Device according to claim 1, wherein a controller and analyzer unit is provided which controls individual functions of said device in compliance with a definable program sequence.

20. Device according to claim 19, wherein an output signal of an image sensor of an imaging unit for forming an image of said target with light arriving from said target can be applied to said controller and analyzer unit.

21. Device according to claim 1, wherein said device is utilized for adjusting a photodynamic diagnosis system.

22. Device according to claim 1, wherein said device is utilized for adjusting a photodynamic therapy system.

23. Device according to claim 1, wherein said device is used for testing a photodynamic medical system.

24. Device according to claim 1, wherein said device is used for training on a photodynamic medical system.

* * * * *